United States Patent
Bandodkar et al.

(10) Patent No.: US 9,120,717 B2
(45) Date of Patent: Sep. 1, 2015

(54) PROCESS FOR THE CONVERSION OF ISOMERIC MIXTURE OF DICHLORODIPHENYL SULFONES TO CHLOROBENZENE

(75) Inventors: Hemant Ratanakar Bandodkar, Thane West (IN); Dilip Chandrakant Sawant, Dombivli East (IN)

(73) Assignee: HEMANT RATANAKAR BANDODKAR, Thane West (IN)

( * ) Notice: Subject to any disclaimer, the term of this patent is extended or adjusted under 35 U.S.C. 154(b) by 0 days.

(21) Appl. No.: 14/368,955

(22) PCT Filed: Apr. 12, 2012

(86) PCT No.: PCT/IB2012/000731
§ 371 (c)(1),
(2), (4) Date: Jun. 26, 2014

(87) PCT Pub. No.: WO2013/153412
PCT Pub. Date: Oct. 17, 2013

(65) Prior Publication Data
US 2014/0364659 A1  Dec. 11, 2014

(51) Int. Cl.
*C07C 17/00* (2006.01)
*C07C 17/361* (2006.01)
*C07C 315/00* (2006.01)

(52) U.S. Cl.
CPC ............ *C07C 17/361* (2013.01); *C07C 315/00* (2013.01)

(58) Field of Classification Search
CPC .............................. C07C 17/361; C07C 25/06
USPC .............................. 568/34, 35; 570/201, 206
See application file for complete search history.

(56) References Cited

U.S. PATENT DOCUMENTS

| 4,983,773 | A | 1/1991 | Stumpp et al. |
| 2011/0218357 | A1 | 9/2011 | Deck et al. |
| 2014/0323765 | A1* | 10/2014 | Reichle et al. ............ 568/34 |

FOREIGN PATENT DOCUMENTS

GB  2476147  6/2011

OTHER PUBLICATIONS

International Search Report from International Application No. PCT/IB2012/000731 mailed Jan. 17, 2013.

* cited by examiner

*Primary Examiner* — Jafar Parsa
(74) *Attorney, Agent, or Firm* — Merchant & Gould P.C.

(57) ABSTRACT

The invention relates to a process for the single step conversion of isomeric mixture of dichlorodipheriyi sulfones to chlorobenzene. The invention further relates a process of using dilute sulfuric acid and re-circulating the dilute sulfuric acid.

8 Claims, No Drawings ized with aqueous alkali solution and washed with water and distilled to obtain 188 g chlorobenzene with 0.79% moisture. The yield of chlorobenzene recovery is 83.55% based on isomeric mixture of dichlorodiphenyl sulfone. 285 g residual spent acid collected containing 59.67% w/w sulfuric acid.

PROCESS FOR THE CONVERSION OF ISOMERIC MIXTURE OF DICHLORODIPHENYL SULFONES TO CHLOROBENZENE

This application is a National Stage Application of PCT/IB2012/000731, filed 12 Apr. 2012 which application is incorporated herein by reference. To the extent appropriate, a claim of priority is made to the above disclosed application.

The invention relates to an economical and environmentally friendly process for the single step conversion of isomeric mixture of dichlorodiphenyl sulfones to chlorobenzene.

Isomeric mixture of dichlorodiphenyl sulfone is a obtained as a by product in production of 4,4'-dichlorodiphenyl sulfone which is commercially produced by various known process such as:

Reaction of monochlorobenzene with dimethyl pyrosulfate and sulfur trioxide in presence or absence of catalyst, Reaction of 4-chlorobenznesulfonic acid and monochlorobenzene in sulfuric acid in presence or absence of catalyst, Friedel-crafts reaction of 4-chlorobenzenesulfonyl chloride and monochlorobenzene in the presence of ferric chloride as a catalyst The isomeric mixture produced in these processes contain 4,4'-dichlorodiphenyl sulfone; 3,4'- and 2,4'-isomers of which 4,4'-dichlorodiphenyl sulfone is the commercially useful product. The residue after isolation of 4,4'-dichlorodiphenyl sulfone comprising of a mixture of 3,4'- and/or 2,4'- and/or 4,4'-dichlorodiphenyl sulfone is generally converted to isomeric mixture of Dihydroxydiphenyl sulfones or isomeric mixture of Diaminodiphenyl sulfones. This is both cost and time intensive and provides no added value. This also reduces the yield of the process of manufacture of 4,4'-dichlorodiphenyl sulfone based on chlorobenzene consumed.

It is desirable to decisively reduce and/or eliminate these intermediates.

UK Patent Application GB 2476147A describes a process for conversion of isomeric mixture of dichlorodiphenyl sulfones to commercially viable products such as diphenyl sulfone, 2-aminodiphenyl sulfone, 2,4'-dihydroxydiphenyl sulfone and 4,4'-dihydroxydiphenyl sulfone.

US Patent Applications 2011/0218357 A1 describes a process for conversion of isomeric mixture of dichlorodiphenyl sulfones to mixture of 2-, 3- and 4-chlorobenzenesulfonic acid and their subsequent conversion 2- and/or 3-chlorobezenesulfonic acid to 4-chlorobenzenesulfonic acid.

The present invention addresses some of the shortcomings in the prior art by converting these intermediates to chlorobenzene for reuse in the process of 4,4'-dichlorodiphenyl sulfone.

OBJECTS OF THE INVENTION

It was an object of the present invention to provide a process of converting isomeric mixture of dichlorodiphenyl sulfones to chlorobenzene.

It is another object of the invention is to re-circulate the chlorobenzene in the production process of 4,4'-dichlorodiphenyl sulfone.

It is another object of the invention to re-circulate the spent (residual) sulfuric acid in the process of conversion of isomeric mixture of dichlorodiphenyl sulfone to chlorobenzene.

It is yet another object of the invention to provide a "green process" by substantially reducing effluent production and treatment.

The process of the invention may be carried out in the manner described below:

The process of the invention can be carried out batch wise in a stirred vessel or semi-continuously or continuously in continuous flow reactors packed with packing elements.

Thus in accordance with the invention the isomeric mixture of dichlorodiphenyl sulfone is convened to chlorobenzene in a single step reaction and reused in the process of 4,4'-dichlorodiphenyl sulfone comprising:

1. Treating the isomeric mixture of dichlorodiphenyl sulfone with dilute sulfuric acid,
2. Azeotropically distilling of the reaction product to obtain chlorobenzene,
3. Neutralizing the chlorobenzene with aqueous alkali solution and distilling the same obtain significantly moisture free chlorobenzene,
4. Reusing the residual acid of step 2 and re-circulating chlorobenzene in the process for production of 4,4'-dichlorodiphenyl sulfone.

Sulfuric acid used in the process is 30 to 85% w/w

The molar ratio of isomeric mixture of dichlorodiphenyl sulfone with sulfuric acid is 1:0.25 to 1:7, Preferably 1:0.50 to 1:7

The reaction temperature is 170 to 260° C., preferably 200 to 240° C. In one of the embodiments the reaction is carried out under reduced pressure at <170° C. The invention is now illustrated with reference to the following non-limiting examples.

EXAMPLE 1

Conversion of Isomeric Mixture of Dichlorodiphenyl Sulfone to Chlorobenzene by Reacting with 60% w/w Sulfuric Acid at 210-230° C. with Molar Ratio of 1:1.4

287 g (1 mole) of isomeric mixture of dichlorodiphenyl sulfone containing 33.41% 4,4'-; 11.75% 3,3'-; and 52.40% 2,4'-isomer, was added to 230 g sulfuric acid, 60% w/w (1.4 mole) under stirring and heated to 220° C., and azeotropic mixture of water and chlorobenzene is collected in Dean and Stark water trap. Reaction is continued at the end of the chlorobenzene; 207 g crude chlorobenzene is collected. The obtained chlorobenzene is acidic in nature hence was neutral-

EXAMPLE 2

Conversion of Isomeric Mixture of Dichlorodiphenyl Sulfone to Chlorobenzene by Reacting with 60% w/w Sulfuric Acid at 210-230° C. with Molar Ratio of 1:4.0

287 g (1 mole) of isomeric mixture of dichlorodiphenyl sulfone containing 33.41% 4,4'-; 11.75% 3,3'-; and 52.40% 2,4'-isomer, was added to 650 g sulfuric acid, 60% w/w (4.0 mole) under stirring and heated to 220° C., and Azeotropic mixture of water and chlorobenzene is collected in Dean and Stark water trap. Reaction is continued at the end of the chlorobenzene; 226 g crude chlorobenzene is collected. The obtained chlorobenzene is acidic in nature hence was neutralized with aqueous alkali solution and washed with water and redistilled to obtain 205 g chlorobenzene with 0.63% moisture. The yield of chlorobenzene recovery is 91.11% based on isomeric mixture of dichlorodiphenyl sulfone. 570 g residual spent acid collected containing 60.57% w/w sulfuric acid.

EXAMPLE 3

Conversion of Isomeric Mixture of Dichlorodiphenyl Sulfone to Chlorobenzene by Reacting with 30% w/w Sulfuric Acid at 210-230° C. with Molar Ratio of 1:4.0

287 g (1 mole) of isomeric mixture of dichlorodiphenyl sulfone containing 33.41% 4,4'-; 11.75% 3,3'-; and 52.40% 2,4'-isomer, was added to 1306 g sulfuric acid, 30% w/w (4.0 mole) under stirring and heated to 220° C., and Azeotropic mixture of water and chlorobenzene is collected in Dean and Stark water trap. Reaction is continued at the end of the chlorobenzene; 221 g crude chlorobenzene is collected. The obtained chlorobenzene is acidic in nature hence was neutralized with aqueous alkali solution and washed with water and redistilled to obtain 203 g chlorobenzene with 0.89% moisture. The yield of chlorobenzene recovery is 90.22% based on isomeric mixture of dichlorodiphenyl sulfone. 553 g residual spent acid collected containing 70.64% w/w sulfuric acid.

EXAMPLES 4 to 30

Several experiments were carried out as per Example 1 except that the mole ratio of isomeric mixture of dichlorodiphenyl sulfone:sulfuric acid was varied from 1:0.5 to 1:7.0 and concentration of sulfuric acid was varied from 30 to 80%.

The results are presented in table 1:

| Exp. No | Conc. of sulfuric acid In % w/w | Molar Ratio DCDPS:$H_2SO_4$ | Chlorobenzene yield in % w/w | % w/w as $H_2SO_4$ in spent acid |
| --- | --- | --- | --- | --- |
| 4  | 30 | 1:0.50 | 86.66 | 69.17 |
| 5  | 30 | 1:0.75 | 87.55 | 74.00 |
| 6  | 30 | 1:1.0  | 83.55 | 71.78 |
| 7  | 30 | 1:1.4  | 88.88 | 77.90 |
| 8  | 30 | 1:1.8  | 92.00 | 79.75 |
| 9  | 30 | 1:5.74 | 87.11 | 79.15 |
| 10 | 30 | 1:7.0  | 90.66 | 78.85 |
| 11 | 60 | 1:0.50 | 93.77 | 77.55 |
| 12 | 60 | 1:0.75 | 92.44 | 75.19 |
| 13 | 60 | 1:1.0  | 84.44 | 68.88 |
| 14 | 60 | 1:1.8  | 86.66 | 68.48 |
| 15 | 60 | 1:5.74 | 87.11 | 78.49 |
| 16 | 60 | 1:7.0  | 84.00 | 78.95 |
| 17 | 80 | 1:0.50 | 88.88 | 76.02 |
| 18 | 80 | 1:0.75 | 85.77 | 59.35 |
| 19 | 80 | 1:1.0  | 88.88 | 80.75 |
| 20 | 80 | 1.1.4  | 87.11 | 80.56 |
| 21 | 80 | 1:1.8  | 87.11 | 76.27 |
| 22 | 80 | 1:4.0  | 91.55 | 80.97 |
| 23 | 80 | 1:5.74 | 88.44 | 81.67 |
| 24 | 80 | 1:7.0  | 91.11 | 80.30 |
| 25 | 70 | 1:1.40 | 89.77 | 75.17 |
| 26 | 70 | 1:1.8  | 87.11 | 61.06 |
| 27 | 70 | 1:4.0  | 92.00 | 73.52 |
| 28 | 70 | 1:1.0  | 88.44 | 70.61 |
| 29 | 50 | 1:4.0  | 93.33 | 69.02 |
| 30 | 40 | 1:4.0  | 86.22 | 78.68 |

The present invention provides an economic and environmentally friendly method for the conversion of isomeric mixture of dichlorodiphenyl sulfone to chlorobenzene and reuse in production process of 4,4'-dichlorodiphenyl sulfone overcoming all the shortcomings of the prior art

The invention claimed is:

1. A single step process for the conversion of an isomeric mixture of dichlorodiphenyl sulfones to chlorobenzene comprising:
    treating the isomeric mixture of dichlorodiphenyl sulfones with 30 to 85% w/w sulfuric acid;
    azeotropically distilling of the result of treating to obtain chlorobenzene;
    neutralizing the chlorobenzene with aqueous alkali solution and distilling the same to obtain significantly moisture free chlorobenzene;
    reusing the residual acid from distilling; and
    re-circulating chlorobenzene in the process for production of 4,4'-dichlorodiphenyl sulfone.

2. The process of claim 1, wherein treating is conducted at 170 to 260° C.

3. The process of claim 1, wherein the molar ratio of isomeric mixture of dichlorodiphenyl sulfones to sulfuric acid is 1:0.25 to 1:7.

4. The process of claim 1, wherein the reaction is carried out at reduced pressure at <170° C.

5. The process of claim 2, wherein treating is conducted at 200 to 240° C.

6. The process of claim 2, wherein treating is conducted with 30 to 80% w/w sulfuric acid.

7. The process of claim 2, wherein treating is conducted with 30, 40, 50, 60, 70, or 80% w/w sulfuric acid.

8. The process of claim 2, wherein treating is conducted with 30 to 60% w/w sulfuric acid.

* * * * *